United States Patent [19]

Mustakallio et al.

[11] 4,299,846
[45] Nov. 10, 1981

[54] DIHYDROXY-ACYLANTHRONES HAVING ANTI-PSORIATIC ACTIVITY

[75] Inventors: Kimmo K. Mustakallio, Helsinki; Aino K. Pippuri, Espoo; Erkki J. Honkanen, Helsinki, all of Finland

[73] Assignee: Orion-yhtyma Oy, Finland

[21] Appl. No.: 133,772

[22] Filed: Mar. 25, 1980

[30] Foreign Application Priority Data

Mar. 29, 1979 [FI] Finland .................................. 791058

[51] Int. Cl.³ ........................ A61K 31/12; C07C 50/18
[52] U.S. Cl. ..................................... 424/331; 260/351
[58] Field of Search ........................ 260/351; 568/326; 424/331

[56]  References Cited

U.S. PATENT DOCUMENTS

| 1,935,928 | 11/1933 | Zahn et al. | 260/351 |
| 2,841,596 | 7/1958 | Stephens | 260/351 |
| 4,007,271 | 2/1977 | Robertson | 260/351 |

OTHER PUBLICATIONS

Van Duuren et al., J. Med. Chem., vol. 21 #1, pp. 26-31, (1978).

*Primary Examiner*—Natalie Trousof
*Assistant Examiner*—James H. Reamer
*Attorney, Agent, or Firm*—Biebel, French & Nauman

[57]  ABSTRACT

New 1,8-dihydroxy-10-acyl-9-anthrones having anti-psoriatic activity are disclosed.

6 Claims, No Drawings

DIHYDROXY-ACYLANTHRONES HAVING ANTI-PSORIATIC ACTIVITY

BACKGROUND OF THE INVENTION 1,8-Dihydroxy-9-anthrone, or anthralin (dithranol), has been used since 1916 for the treatment of psoriasis and certain other skin diseases. There are, however, several adverse effects involved in the use of anthralin. First, anthralin has a strong inflammatory effect on the skin. Furthermore, it stains skin, hair and clothes a strong purplish brown colour, a factor which limits its use esthetically. In order to eliminate these adverse effects, certain derivatives have been prepared from anthralin, e.g. 1,8,9-triacetoxy-anthracene (Exolan ®). Exolan ® does not stain or inflame the skin to the same degree as anthralin. Its anti-psoriatic action is, however, to such a considerable degree lower that it has not been used extensively in medicine.

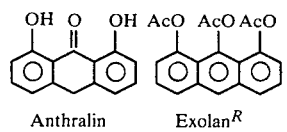

Anthralin   Exolan$^R$

SUMMARY OF THE INVENTION

It has surprisingly been observed that compounds according to the general formula I, 1,8-dihydroxy-10-acyl-9-anthrones,

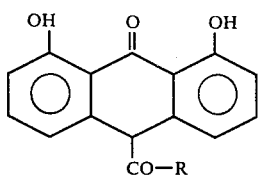

where R represents a lower alkyl group ($C_2$-$C_4$), have considerably reduced inflammatory and staining properties. The anti-psoriatic action of the compounds according to the invention is, however, still quite high and they thus offer considerable advantages in the treatment of psoriasis, as compared with anthralin and Exolan ®. Previously known is a compound according to the general formula I, where R=methyl (J. Med. Chem 21, 1978, 26). There has been no suggestion, however, that this compound has an anti-psoriatic effect.

New 1,8-dihydroxy-10-acyl-9-anthrones according to formula I and according to the invention can be prepared by a method analogous to the method by which the above known compound, where R=methyl, has been prepared, and this is done by allowing an aliphatic acid chloride, R-COCl, where R is the same as above, to react with anthralin in the presence of an organic amine, e.g. pyridine, in an inert solvent, such as benzene, at the return condenser temperature, using a reactio period of 10-20 hours.

The new anthrone derivatives according to the invention can be used, for example, in the form of vaselin or paraffin-based creams, in which the concentration of the active ingredient can vary from 0.5% to 5%.

DESCRIPTION OF THE PREFERRED EMBODIMENT

The following examples illustrate the invention.

EXAMPLE 1

1,8-dihydroxy-10-propionyl-9-anthrone.

24.9 g (0,269 moles) propionyl chloride is added, while stirring, to a mixture containing 50.9 g (0,225 moles) anthralin in 1575 ml of benzene and 27.5 ml of pyridine. The reaction mixture is cooked using a return condenser for 20 hours while stirring. The solution is filtered and the filtrate is evaporated dry under a lowered pressure. The residue is crystallized out from acetic acid. Yield 27.6 g (43.5% of the theoretical). M.p. = 149°–154° C.

$^1$H-NMR (CDCl$_3$): $\delta$=12.28 (s, 2H), 6.85–7.70 (m, 6H), 5.20 (s, 1H), 2.09 (q, 2H, J=7Hz), 0.81 (t, 3H=7Hz).

EXAMPLE 2

1,8-dihydroxy-10-butyryl-9-anthrone. 28.6 g (0.27 moles) butyryl chloride is added, while stirring, to a mixture containing 50.9 g (0.225 moles) anthraline in 1575 ml benzene and 27.5 ml pyridine. The reaction mixture is cooked using a return condenser for 10 hours while stirring. The solution is filtered and the filrate is evaporated dry under a lowered pressure. The residue is crystallized out from acetic acid. Yield 17.0 g (25.5% of the theoretical).

M.p.=138°–142° C.

$^1$H-NMR (CDCl$_3$): $\delta$=12.23 (s, 2H), 6.77–7.65 (m, 6H), 5.15 (s, 1H), 2.00 (t, 2H, J=7Hz), 1.34 (m, 2H), 0.60 (t, 3H, J=7Hz).

EXAMPLE 3

1,8-dihydroxy-10-vareryl-9-anthrone. 3.4 g (0.028 moles) valeryl chloride is added, while stirring, to a mixture containing 5.34 g (0.0236 moles) anthralin in 165 ml benzene and 2.9 ml pyridine. The reaction mixture is cooked using a return condenser for 18 hours while stirring. The solution is filtered and the filtrate is evaporated dry under a lowered pressure. The residue is crystallized out from acetic acid. Yield 1.56 g (21.3% of the theoretical). M.p.=124°–128° C.

$^1$H-NMR (CDCl$_3$): $\delta$=12.53 (s, 2H), 6.92–7.78 (m, 6H), 5.26 (s, 1H), 1.96 (t, 2H, J=7Hz), 0.68–1.38 (m, 7H).

What we claim is:

1. A 1,8-dihydroxy-10-acyl-9-anthrone composition for use in the treatment of psoriasis comprising a compound of the formula

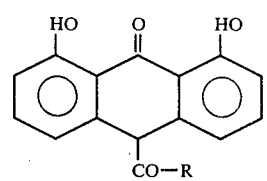

where R represents an alkyl group containing 2–4 carbon atoms and a pharmaceutically acceptable carrier.

2. The composition of claim 1 wherein R represents an alkyl group containing 2 carbon atoms.

3. The composition of claim 1 wherein R represents an alkyl group containing 3 carbon atoms.

4. The composition of claim 1 wherein R represents an alkyl group containing 4 carbon atoms.
5. A process which comprises applying to the skin a composition containing a compound of the formula
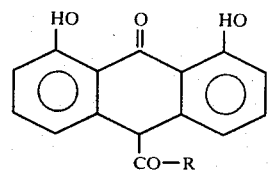
where R is an alkyl group containing 2–4 carbon atoms in a pharmaceutically acceptable carrier.
6. The process of claim 5 wherein said skin is psoriatic.
* * * * *